US006798525B1

(12) United States Patent
Willing

(10) Patent No.: US 6,798,525 B1
(45) Date of Patent: Sep. 28, 2004

(54) SYSTEM FOR INSPECTING MATT, FLAT AND/OR SLIGHTLY CURVED SURFACES

(76) Inventor: Achim Willing, Doschendorf 4, D-96110 Schesslitz-Doschendorf (DE)

( * ) Notice: Subject to any disclaimer, the term of this patent is extended or adjusted under 35 U.S.C. 154(b) by 115 days.

(21) Appl. No.: 10/069,860

(22) PCT Filed: Aug. 24, 2000

(86) PCT No.: PCT/EP00/08282

§ 371 (c)(1), (2), (4) Date: May 10, 2002

(87) PCT Pub. No.: WO01/16584

PCT Pub. Date: Mar. 8, 2001

(30) Foreign Application Priority Data

Aug. 28, 1999 (DE) .......................................... 199 41 028

(51) Int. Cl.[7] .............................................. G01B 11/30
(52) U.S. Cl. ...................................................... 356/600
(58) Field of Search .......................... 356/237.1, 237.2, 356/600, 601, 612, 445, 446

(56) References Cited

U.S. PATENT DOCUMENTS 2,574,031 A * 11/1951 Gretener ..................... 362/224
2,625,646 A * 1/1953 Goebel ....................... 362/224
3,866,036 A * 2/1975 Taltavull ..................... 362/224
5,237,404 A 8/1993 Tanaka et al.
5,309,329 A * 5/1994 Thiel et al. ................... 362/17
5,414,518 A * 5/1995 Yazejian ..................... 356/613
5,424,835 A * 6/1995 Cosnard et al. ............. 356/606
5,570,239 A * 10/1996 Raimondi ................... 359/873
5,627,646 A 5/1997 Stewart et al.
6,278,517 B1 * 8/2001 Willing .................. 356/237.2

FOREIGN PATENT DOCUMENTS

DE 40 12 372 A1 10/1991
EP 0 374 977 A1 6/1990
EP 0 374 977 B1 11/1993
WO WO 9808078 A1 2/1998

* cited by examiner

*Primary Examiner*—Michael P. Stafira
(74) *Attorney, Agent, or Firm*—Marshall & Melhorn, LLC

(57) ABSTRACT

A system for inspecting matt, flat and/or slightly curved surfaces in order to identify defects includes an illumination device which irradiates the surface to be inspected at flat angles and has the following features. The illumination device is formed from a plurality of elongated luminous surfaces which are disposed substantially parallel to one another. The light distribution of the respective elongated luminous surfaces is tightly concentrated in planes which lie transversely with respect to the longitudinal direction of the respective surface, in such a way that a substantially sheet-type light distribution is produced which covers the surface portion to be inspected. The observer is located within or at least in the proximity of the angle predetermined by reflection of the light radiated by the at least one elongated luminous surface on the surface portion to be inspected.

16 Claims, 2 Drawing Sheets

SYSTEM FOR INSPECTING MATT, FLAT AND/OR SLIGHTLY CURVED SURFACES

BACKGROUND OF THE INVENTION

1. Field of the Invention

The invention relates to a system for inspecting matt, flat and/or slightly curved surfaces in order to identify defects which are associated with a modification of the course of the surface, especially for checking flat/unlacquered shell bodywork.

2. Discussion of Related Art

Systems for inspecting matt, flat and/or curved surfaces in order to identify surfaces are known, which have surfaces radiating strip-shaped light, by means of which surfaces unlacquered metal and plastics material surfaces are sampled for topographical defects in a direction parallel with the surface. This requires incident light radiation at very flat radiation angles of approximately 5 to 10°, because at these angles the surfaces reflect in a very directed manner, whilst at steeper angles they predominantly reflect in a diffuse manner. Such illumination strips are suitable only for small surface portions, or means have to be provided with which the strips can be moved relative to the surface (WO 98/15815). If, however, a plurality of strips are lined up beside one another to illuminate larger surfaces, surface portions of the surface to be sampled which are located closer to the lights are illuminated at undesirably steep angles. This leads to masking of defects and identifiable colours and colour effects which would normally be recognisable when associated with the luminous strip. Furthermore the problem of direct dazzling occurs since the lights do not only radiate in the desired directions onto the surface as a result of their light distribution which is too wide.

OBJECT OF THE INVENTION

The object underlying the invention, therefore, is to create a system for inspecting matt, flat and/or slightly curved surfaces which always creates the same illumination conditions over a surface of any size to be sampled, the light distribution of the illumination being intended to be suitable for making topographical defects of an otherwise continuous surface clearly recognisable, the light radiation being intended to be limited to the solid angle required to illuminate the surface, in order to avoid dazzling when the light-radiating surface is viewed directly. At the same time, the luminous device used should be simple in its structure.

This object is accomplished according to the invention by the features of the main claim.

BRIEF SUMMARY OF THE INVENTION

According to the invention the illumination device comprises a plurality of elongated luminous surfaces, disposed substantially parallel to one another and possessing substantially all the same light distribution, which is tightly concentrated in planes which lie transversely with respect to the longitudinal direction of the surfaces, with an aperture angle which is smaller than 15°, preferably 5°, and by even greater preference smaller than 2°, such that a substantially sheet-form light distribution is produced which covers the surface element to be inspected on the surface. In planes in the longitudinal direction of the surfaces, the illumination device has in each case a widely radiating light distribution. The illumination device is so disposed that the angle between the normal line of the inspected surface element and the connecting line between the inspected surface element and any point on the elongated luminous surface is greater than roughly 60°, preferably however 75°, and the observer, i.e. a person or a camera or the like, is located within or at least in the proximity of the at least one elongated strip illuminating by reflection of the sheet-type light distribution on the surface portion to be inspected. By means of this system, illumination is achieved which does not cause any inadvertent dazzling when the light-radiating surfaces are viewed directly, and which permits good detectability of defects which are connected with a modification of the course of the surface.

With the same illumination principle, the position of the observer can be altered by optical means such as mirrors, retro-reflective foils or prisms.

Through the measures quoted in the subordinate claims, advantageous developments and improvements are possible.

Preferably the illumination device used has a light-radiating original surface, in front of which a bundle with parallel lamellae surfaces is disposed, the main radiation direction of the original surface radiating light through the lamellae arrangement. The original surface has uniform luminance distribution and radiates light in a larger solid angle area than the totality of the elongated light-radiating surfaces at the end of the lamellae bundle. The lamellae arrangement is preferably so dimensioned in respect of its geometry, i.e. spacing and depth, that diagonally to the lamellae surface the aperture angle is smaller than 15°, preferably smaller than 5°, and by particular preference smaller than 2°.

The original surface is preferably formed by elongated light sources lying beside one another or also by at least one elongated light source which is surrounded by a trough-like reflector. The elongated lamps can be for example fluorescent lamps or linear incandescent lamps, the light distribution of which is automatically widespread in planes parallel to the lamp axis. It is propitious to use only a few lamps and so to align their light distribution by reflectors or lenses that the solid angle region over which the radiation falls is greater than the solid angle required by the entire illumination device.

According to the invention, the surfaces of the lamellae scatter light in a diffuse manner with a is smaller proportion of directed reflection, or they reflect in a directed manner with a small reflection factor. A gap-free illumination in a narrow angle range is produced according to the invention with surfaces which at very flat incident light angles have a high degree of directed reflection and at steeper incident light angles pass into diffuse reflection. These are, for example, lacquered surfaces or metallic surfaces. The surfaces of the lamellae are preferably black or grey.

In a preferred embodiment, the lamellae can also be disposed either on one or on both sides of light guide plates so as to be optically dense, filling the gaps between the plates and having polished light entrance and exit surfaces.

BRIEF DESCRIPTION OF THE DRAWINGS

Embodiments of the invention are represented in the drawing and are described in greater detail in the following description. The figures show.

DESCRIPTION OF THE PREFERRED EMBODIMENT

Figure 1:
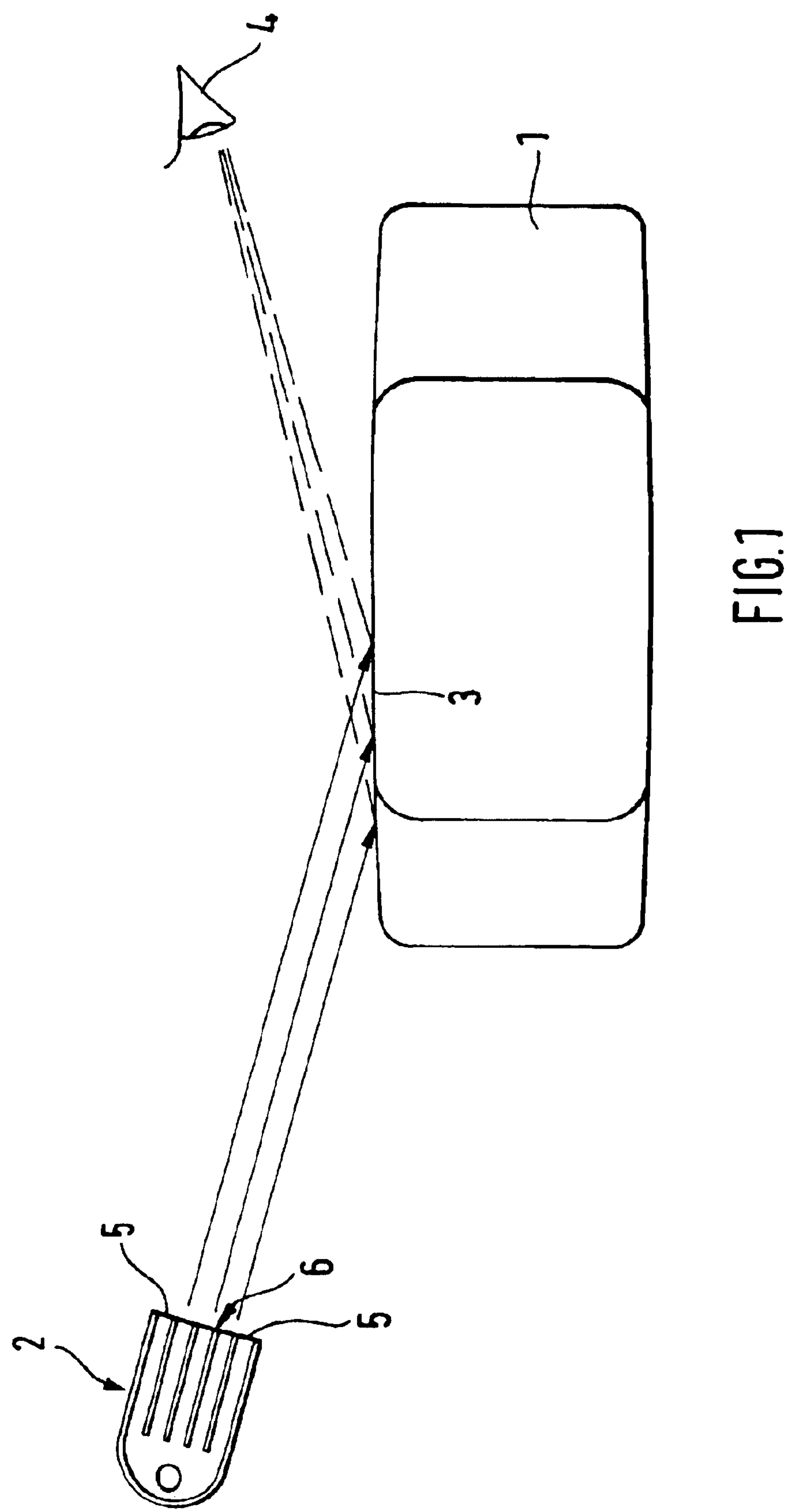
FIG. 1: a schematic front elevation of the system according to the invention.
Figure 4:
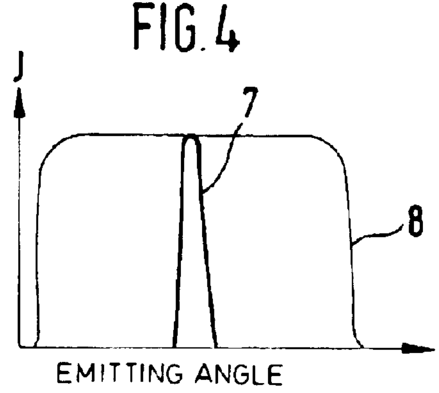
FIG. 4: a representation of light distributions, as used in an illumination device according to the invention.
Figure 5:
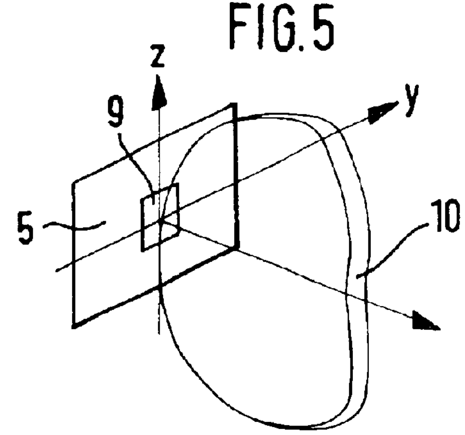
FIG. 5: the representation of a sheet-type light distribution according to FIG. 4, FIG. 6: ray paths at the lamellae used in the illumination device according to the invention.

In FIG. 1 is represented a system for inspecting the side surfaces of shell bodywork 1, in which system at least one illumination device 2 illuminates a flat or slightly curved surface 3, which is roughly perpendicular in the embodiment shown, and an observer 4 inspects the illuminated surfaces for defects which are connected with a modification of the course of the surface, i.e. topographical defects. The observer can here be a person; a camera or some other sensor arrangement for detecting the image of the surface can also be provided. Illumination by the illumination device 2 takes place at a flat angle smaller than 30°, and preferably smaller than 15°, i.e. greater than 60° to the normal line of the surface 3, preferably greater than 75°. The observer 4 is located within or in the proximity of the angle predetermined by the reflection of the light rays of the illumination device 2, i.e. approximately in the mirror angle. The illumination device 2 is represented in various embodiments in FIGS. 2 and 3, the light distribution of the illumination device being recognisable in FIGS. 4 and 5. The illumination device 2 has a plurality of elongated luminous surfaces 5 lying beside one another, which together form the light exit surface 6 of the illumination system 2. The longitudinal direction of the luminous surfaces 5 is perpendicular in FIG. 1 to the page plane, and in an identical longitudinal direction, i.e. in a longitudinal direction parallel to the longitudinal direction of the luminous surfaces 5, lies the surface to be inspected 3. The light distribution of each luminous surface 5 is represented in FIG. 4 and FIG. 5, the light distribution 7 showing the radiation in planes which lie transversely with respect to the longitudinal direction of the luminous surface 5, whilst the light distribution 8 represents the widespread radiation in planes in the longitudinal direction of the luminous surface 5. One surface element 9 of the luminous surface 5 is represented in FIG. 5 in a small x-, y- and z-coordinate system, which delivers a light distribution according to FIG. 4. Here z represents the longitudinal direction and it can be recognised that the light is tightly concentrated in planes which lie transversely with respect to the longitudinal direction, such that a substantially sheet-type light distribution 10 is produced. Here the aperture angle in the planes which lie transversely with respect to the longitudinal direction is smaller than 15°; an aperture angle of smaller than 5° is better, however preferably smaller than 2°.

The luminous surfaces 5, as shown in FIG. 1, have such a sheet-type light distribution 10, the light thus being radiated in narrow strips onto the surface 3. These narrow strips lie on the surface 3 transversely with respect to the longitudinal direction of the surface, and they preferably only overlap one another slightly. The strips are viewed by the observer 4 at an angle which deviates slightly from the mirror angle but is in the vicinity of same since in this case topographical details can be recognised even better.

Figure 2:
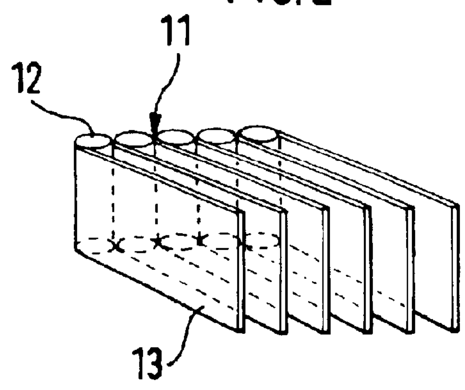
FIG. 2: a perspective view of an illumination device which is used in the system according to the invention.

In FIG. 2 is represented an illumination device 2, the luminous original surface 11 of which is formed from a plurality of lamps 12 aligned parallel to one another and at a small spacing from one another. The luminous original surface 11 has a uniform luminous distribution, the lamps being for example elongated fluorescent lamps or linear incandescent lamps. In front of the lamps is disposed a plurality of lamellae 13 aligned parallel and forming a lamellae bundle, which as a result of their geometry, i.e. their mutual spacing and their depth, form the desired aperture angle of smaller than 15°, better 5°, preferably 2°.

Figure 3:
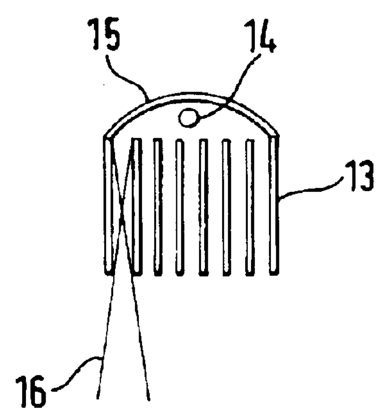
FIG. 3: a section through a further embodiment of an illumination device, as is used in the system according to the invention.

In FIG. 3 is represented a further embodiment of the illumination device used in FIG. 1, and this in section, an elongated light source 14 also being used here which is surrounded by a reflector which is configured trough-like for example. Here the inner side of the reflector 5 facing the lamp 14 forms the original surface, the luminance of which is uniformly distributed. In front of the reflector 5 is arranged again a bundle of lamellae 13, the aperture angle of a luminous surface corresponding to the light distribution according to FIG. 5 being given by the light rays 16. The illuminated surface is in this case interrupted again and again in oblique directions by the lamellae 13.

Figure 6:
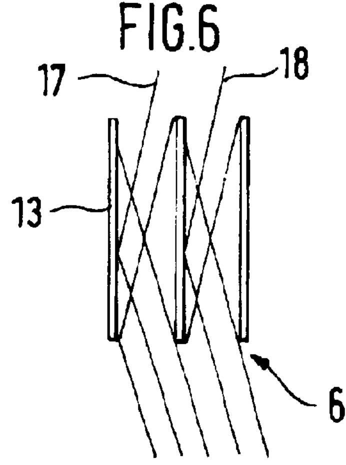

FIG. 6 shows a continuously illuminated light-radiating surface 6, formed from two partial surfaces, between the lamellae 13, of which only three are shown here. This uniform light-radiating surface 6 is produced by directed reflection of the light rays 17, 18 at the lamellae 13 at flat angles, such that the surface to be inspected is also illuminated without any gaps.

Figure 7:
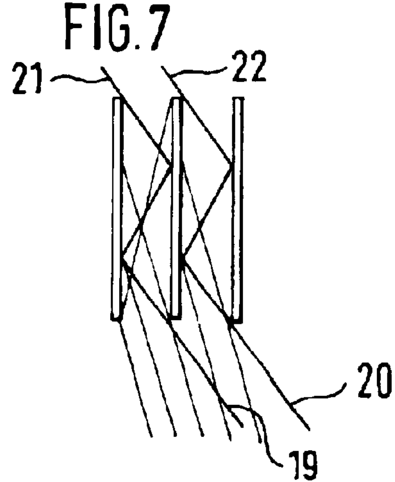
FIG. 7: ray paths according to FIG. 6 at other angles of incidence.

In FIG. 7, on the other hand, steeper light rays 19, 20 are represented, from the direction of which the lamellae optical system now appears dark. Rays 19 and 20 are produced by multiple reflections of rays 21 and 22, which moreover impinge at steeper angles of light incidence, at which the degree of the directed reflection decreases, such that rays 19 and 20 have practically no luminance anymore. This means that the observer 4, if he inadvertently looks directly into the illumination device 2 according to FIG. 1, is not dazzled. The surfaces of the lamellae are preferably black.

In a further embodiment of the illumination device, for example according to FIG. 3, between the lamellae 13 are provided light-guiding transparent plates, i.e. the gaps between the lamellae 13 are filled with a light-guiding transparent medium, the lamellae surface being connected at least on one side in an optically dense manner to the transparent medium or respectively the light guide plates. Here the light guide plates have polished light entrance and exit surfaces.

The abstract forms part of the disclosure of the present invention, i.e. part of the description.

What is claimed is:

1. A system for inspecting matt, flat and/or slightly curved surfaces in order to identify defects which are associated with a modification of the course of the surface, in particular for examining matt unlacquered shell bodywork, in which system an illumination device irradiates the surface to be inspected at flat angles, said device having the following combined features:

the illumination device is formed from a plurality of elongated luminous surfaces which are disposed substantially parallel to one another, the angle between the normal line of an inspected surface element on the surface and the connecting line between the inspected surface element and a point on one of the elongated luminous surfaces is greater than approximately 60°, the light distribution of the respective elongated luminous surfaces is tightly concentrated in planes which lie transversely with respect to the longitudinal direction of the respective surface, with an aperture angle which is smaller than 15°, in such a way that a substantially sheet-type light distribution is produced which covers the surface portion to be inspected, and the observer is located within or at least in the proximity of the angle predetermined by reflection of the light radiated by the at least one elongated luminous surface on the surface portion to be inspected.

2. A system according to claim 1, wherein the aperture angle of the sheet-type light distribution is smaller than 5°, preferably smaller than 2°.

3. A system according to claim 1, wherein the angle between the normal line of an inspected surface element and the incident light ray of the elongated luminous surface is greater than 75°.

4. A system according to claim 1, wherein the longitudinal direction of the luminous surfaces is substantially parallel to the longitudinal direction of the surface to be inspected which is illuminated by this luminous surface.

5. A system according to claim 1, wherein each surface portion to be inspected is illuminated by at least one elongated luminous surface from its entire length and breadth.

6. A system according to claim 1, wherein the luminous elongated surfaces so disposed beside one another are so arranged in respect of their concentration that they illuminate adjacent surfaces to be inspected in the same alignment.

7. A system according to claim 1, wherein the illumination device has a light-radiating original surface which has a substantially uniform luminance distribution and wherein there is arranged in front of this original surface a plurality of lamellae which are substantially parallel to one another and which determine the desired aperture angle on the basis of their geometry.

8. An illumination device according to claim 7, wherein the surfaces of the lamellae have a high reflection factor of the directed reflection at flat light entrance angles, and at steep light entrance angles reflect predominantly in a diffuse manner.

9. A system according to claim 7, wherein the surface of the lamellae is black.

10. A system according to claim 7, wherein the gaps between the lamellae are filled with a light-guiding transparent medium, and in that the surface of the lamellae is connected to the medium in an optically dense manner at least on one side.

11. A system according to claim 1, wherein the observer is a person, a camera or some other sensor arrangement for capturing an image.

12. A system according to claim 1, wherein the illumination device has a light-radiating original surface which has a substantially uniform luminance distribution the light-radiating original surface radiating at a solid angle which is greater than the solid angle of the radiation of the luminous surfaces.

13. A system according to claim 1, wherein the illumination device has at least one elongated light source, the light distribution of which radiates widely in planes parallel to its axis.

14. A system according to claim 1, wherein the illumination device has a light-radiating original surface which has a substantially uniform luminance distribution whereby the original surface is composed of a plurality of widely radiating, elongated light sources which are disposed beside one another, at least one pair of lamellae being placed in front of each light source.

15. A system according to claim 1, wherein the illumination device has a light-radiating original surface which has a substantially uniform luminance distribution the original surface being formed from at least one elongated light source with a trough-like reflector.

16. A system according to claim 1, wherein the position of the observer can be altered by optical measures such as mirrors, retro-reflective materials or prisms.

* * * * *